United States Patent [19]
Zlotnik et al.

[11] Patent Number: 5,533,705
[45] Date of Patent: Jul. 9, 1996

[54] DRIVE FOR DEODORANT APPARATUS

[75] Inventors: Arnold H. Zlotnik, Pittsburgh; John A. Austin, Bakerstown; Milton Zlotnik, West Homestead, all of Pa.

[73] Assignee: Pestco, Inc., Pittsburgh, Pa.

[21] Appl. No.: 471,960

[22] Filed: Jun. 6, 1995

Related U.S. Application Data

[62] Division of Ser. No. 370,540, Jan. 9, 1995.

[51] Int. Cl.[6] .................................................. F16M 11/00
[52] U.S. Cl. .................. 248/645; 248/222.11; 248/314; 248/674
[58] Field of Search ...................................... 248/558, 645, 248/670, 671, 674, 311.2, 311.3, 314, 223.41, 222.11

[56] References Cited

U.S. PATENT DOCUMENTS

| 1,329,816 | 2/1920 | Winslow | 248/645 X |
|---|---|---|---|
| 3,145,960 | 8/1964 | Langdon | 248/671 |
| 3,207,317 | 9/1965 | Moore et al. | 248/314 X |
| 4,155,528 | 5/1979 | Dawson | 248/674 |
| 4,931,258 | 6/1990 | Zlotnik et al. | 422/124 |
| 5,069,415 | 12/1991 | Mechalas | 248/674 |
| 5,356,105 | 10/1994 | Andrews | 248/674 X |

FOREIGN PATENT DOCUMENTS 1308598  10/1962  France ........................... 248/674

Primary Examiner—Ramon O. Ramirez
Assistant Examiner—Derek J. Berger
Attorney, Agent, or Firm—Hymen Diamond

[57] ABSTRACT

A drive for providing an air stream for generating vapor from a wick or ceramic wafers or discs containing vaporizable deodorant. The drive includes a socket assembly in which a socket for a motor of larger dimensions and a socket for a motor of smaller dimensions are mounted back-to-back. The mounting of the assembly in the deodorant apparatus is reversible so that either socket can receive the corresponding motor for driving the air.

10 Claims, 5 Drawing Sheets

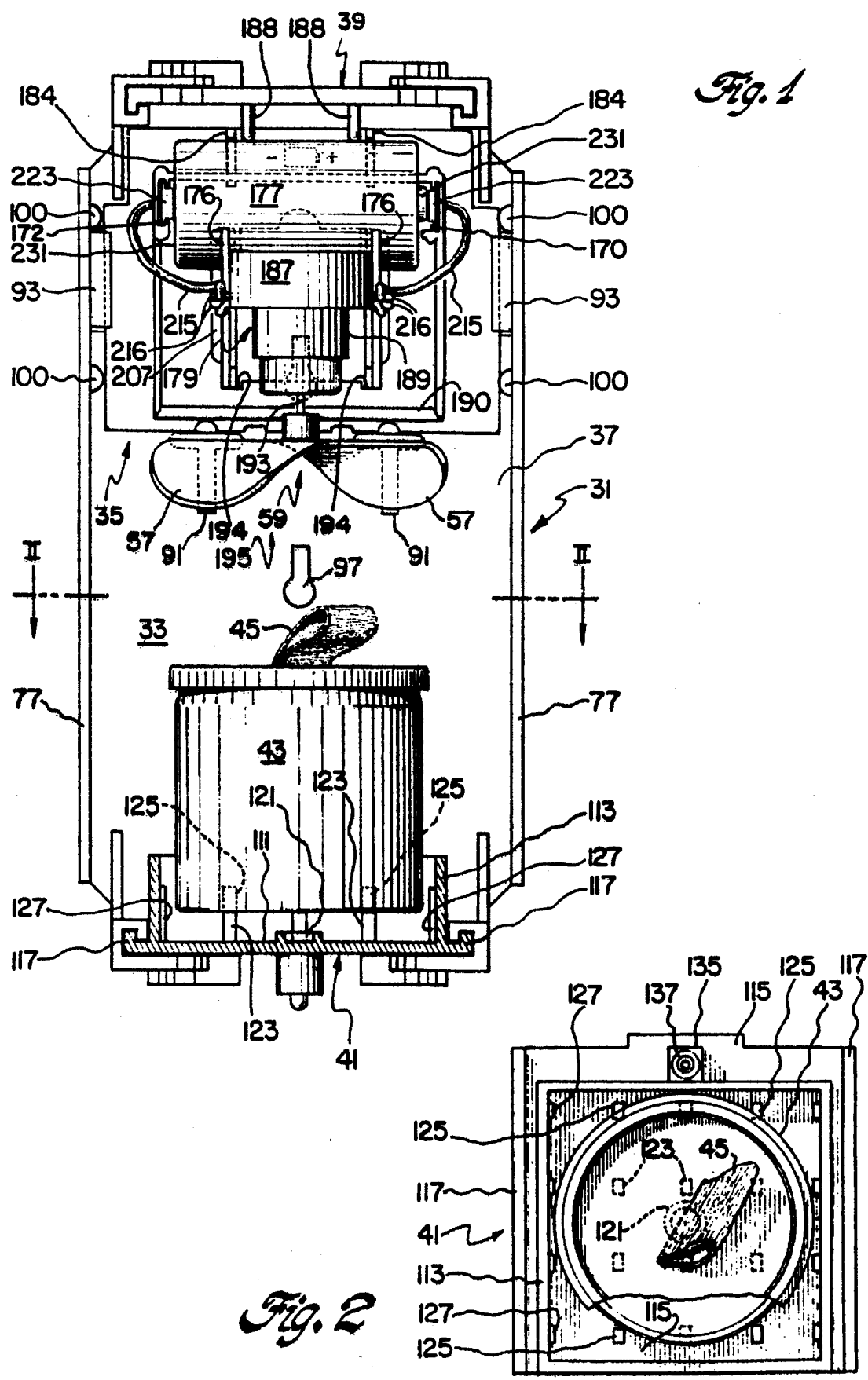

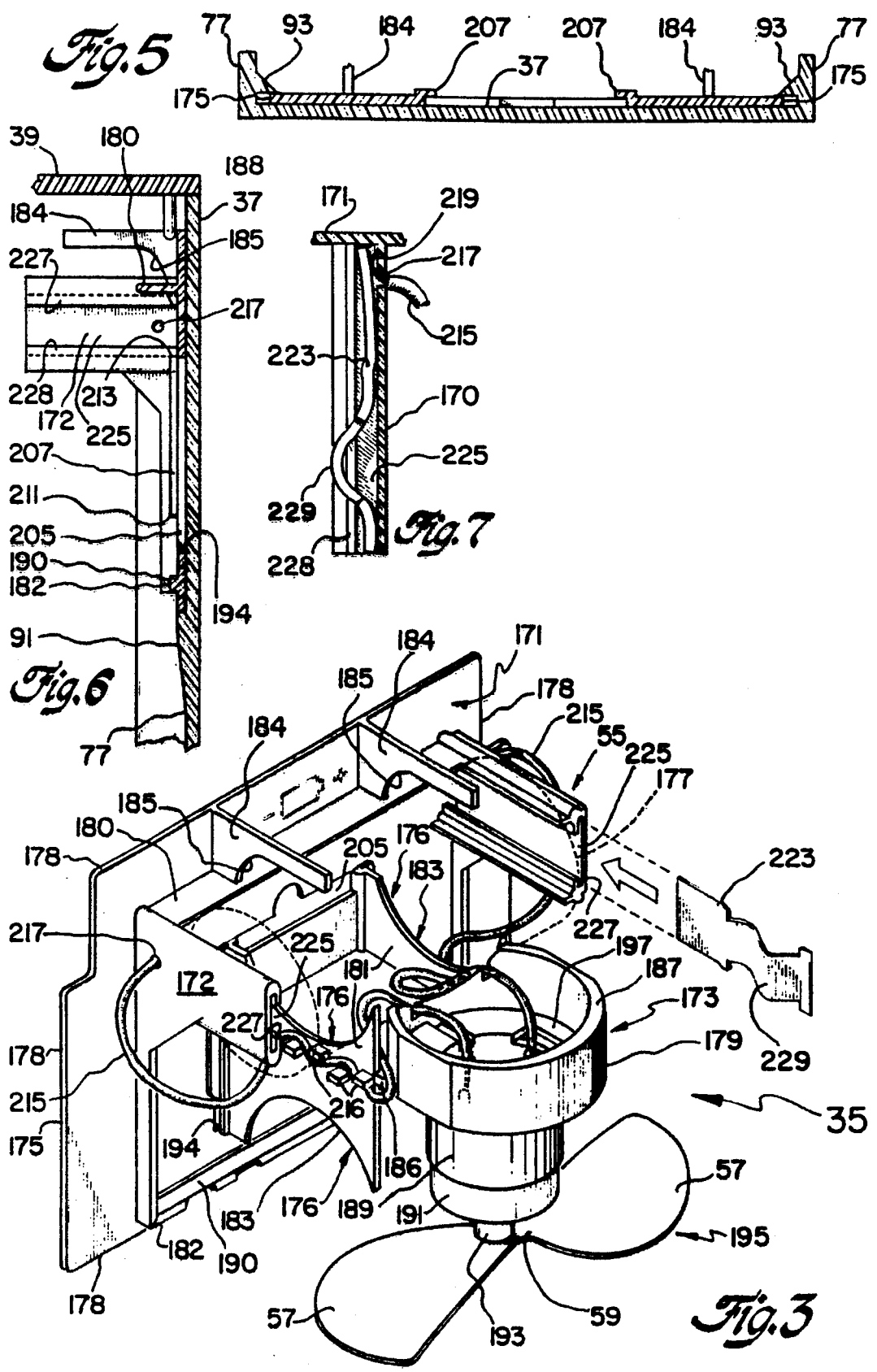

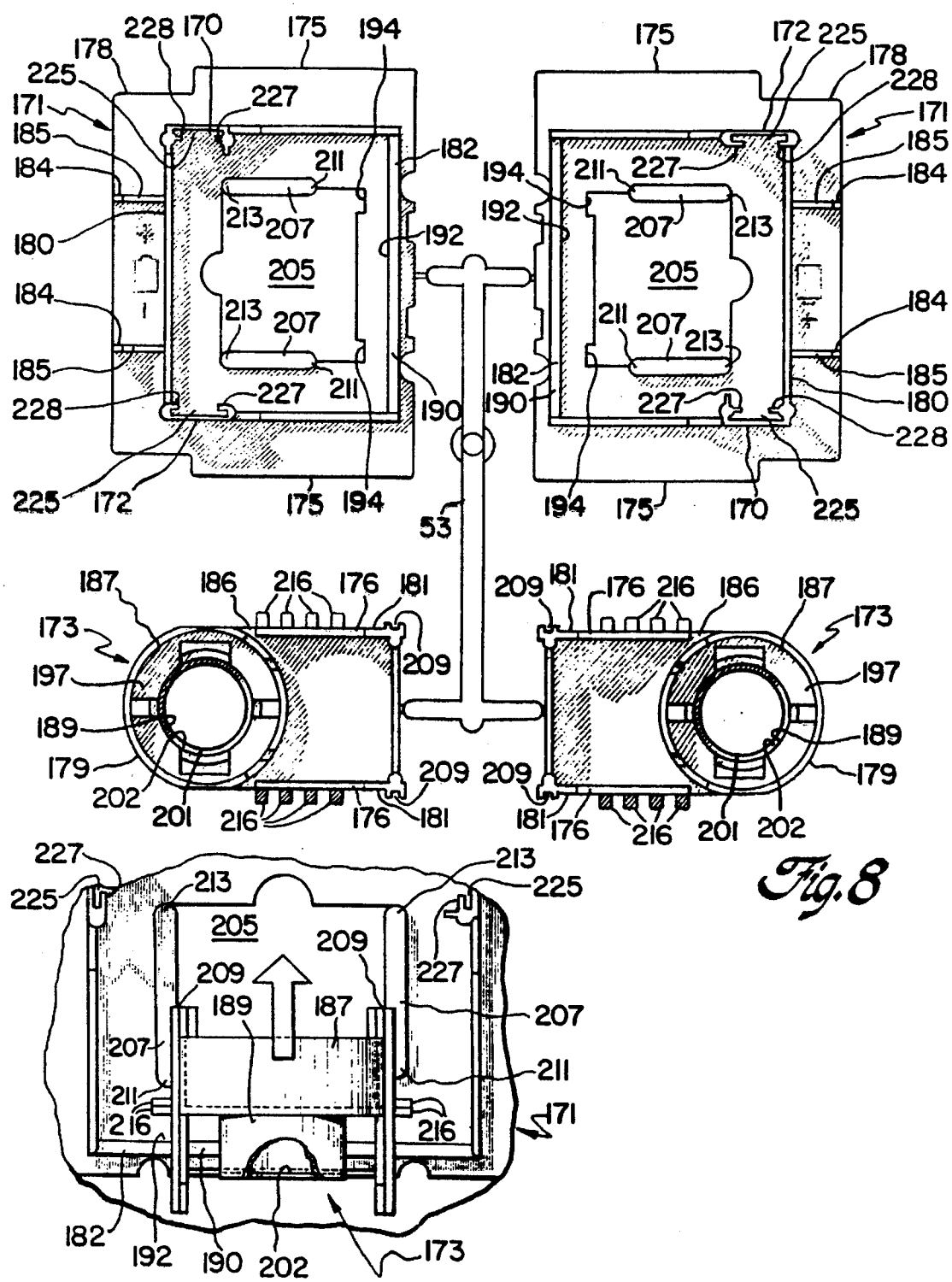

5,533,705

DRIVE FOR DEODORANT APPARATUS

REFERENCE TO RELATED APPLICATION

This application is a division of application Ser. No. 08/370,540, filed Jan. 9, 1995, for INTEGRATED FRAME ASSEMBLY FOR DEODORANT CABINET and assigned to PESTCO, INC. and herein referred to as parent application.

BACKGROUND OF THE INVENTION

This invention relates to deodorizers such as are used to deodorize commodes and urinals, particularly in the toilets of institutions and places frequented by the public, although it may also be used in homes. Particularly, this invention relates to the blower for diffusing a deodorant vapor and specifically for the drive for this blower.

As disclosed in the parent application, there is provided a frame which includes separate back plate, a top member and a bottom member composed of flexible material which are snap locked into a rigid structure. The bottom member is a liquid-tight tray structured to receive and hold various deodorizing devices which are in use. Typically these include a bottle with a valve at its tip for maintaining a measured pool of deodorant or disinfectant liquid, contained in the bottle in the tray, i.e. the bottom member, a can with a wick in its top, porous impregnated ceramic discs, and porous impregnated fibre wafers.

The liquid absorbed by the wick in the can and the porous ceramic discs and porous fibre wafer is vaporized by a stream of air from a blower unit, usually battery driven, which is snap-mounted on the back plate above the tray. The tray has studs for positioning the can and the discs and wafers so that the air from the blower flows freely around these components.

SUMMARY OF THE INVENTION

In accordance with this invention, a motor-blower unit is provided which includes integrated socket structure including sockets readily capable of accommodating motors of different physical dimensions.

Typically, the blower unit includes a motor for driving the blower energized by a battery or other power supply. It is frequently necessary that the blower be driven by motors of physically different dimensions. Prior to this invention, this necessity demanded that deodorizers of different structure be made available to accommodate the motors of different dimensions. Or where an installed deodorizer, for one reason or another, required a motor of different dimensions than the motor installed, it was necessary that extensive changes be made in the installed deodorizer.

It is an object of this invention to provide a deodorizer which shall accommodate motors of different dimensions without requiring extensive restructuring. These sockets for the motors of different physical dimensions are mounted back-to-back on a battery motor bracket which is capable of being reversibly and removably snap-mounted on a support. The support is securely suspended from the back plate. In the socket assembly, the sockets are so structured at their joint that the motor of smaller dimensions can be inserted in its socket through the socket for the motor of larger dimensions.

BRIEF DESCRIPTION OF THE DRAWINGS

For a better understanding of this invention, both as to its organization and as to its method of operation, together with additional objects and advantages thereof, reference is made to the following description taken in connection with the accompanying drawings, in which:

FIG. 1 is a view in front elevation showing a frame assembly in accordance with the invention of parent application having integrated therein apparatus in accordance with this invention;

FIG. 2 a plan view of the lower member of the apparatus own in FIG. 1, taken along line II-II of FIG. 1;

FIG. 3 is a view in isometric showing the complete battery-blower unit in accordance with this invention which is integrated into the back plate of the frame assembly;

FIG. 5 is a view transverse section taken along line V—V of FIG. 4;

FIG. 6 is a view partial longitudinal section taken along line VI—VI of FIG. 4;

FIG. 7 is a fragmental view partly in section showing the connection of a motor terminal wire at its point of contact to the battery with a metal clip and without soldering;

FIG. 8 a plan view showing the blower assembly as it is impleted and removable from twin molds and;

FIG. 9 is a fragmental view in elevation showing how the battery-blower unit is mounted on the support plate;

DETAILED DESCRIPTION OF EMBODIMENT

Figure 4:
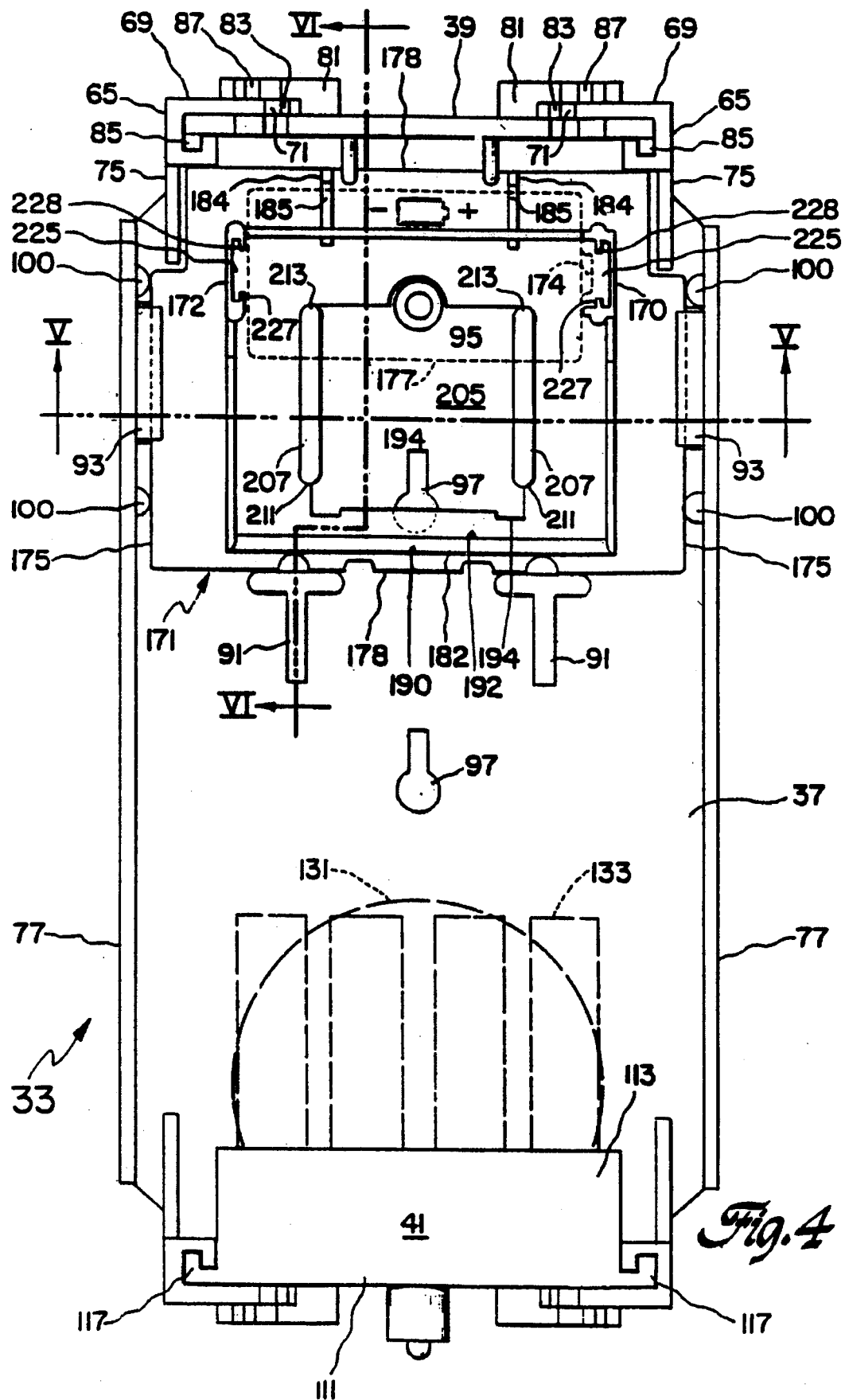
FIG. 4 is a view front elevation of the frame showing the facilities for mounting the battery-blower unit.
Figure 4:
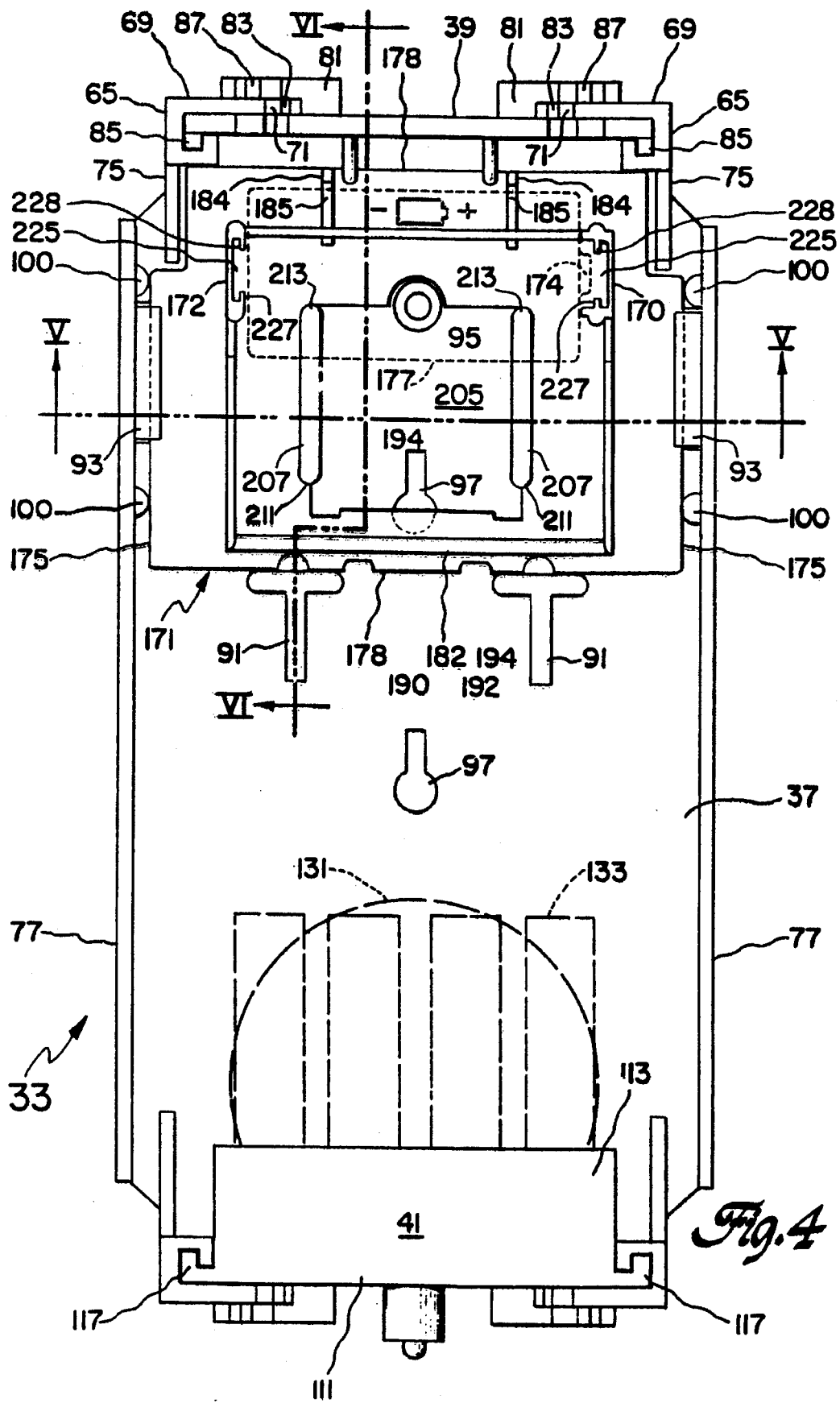

The apparatus disclosed in the drawings is an integrated frame assembly 31 for supporting the housing for containing facilities for dispensing a deodorant or a disinfectant or the like, particularly in the rest rooms of a public institution. The assembly 31 includes a frame 33. The battery-blower unit 35 in accordance with this invention is mounted on the frame 33. The frame 33, also includes a back plate 37, a top member 39 and and a bottom member 41 which is essentially a liquid-tight tray. In FIGS. 1 and 2 a can 43 of a deodorant which has a wick 45 that absorbs the deodorant is shown. The deodorant in the wick is vaporized by a stream of air from the battery-blower unit 35. The can 43 is one of number of facilities for producing a deodorant or like vapor which the apparatus 31 is adapted to process.

The back plate 37 has ramps 91 and runners 93 for securing the battery-blower unit and openings for mounting the frame 31 on a wall. On the internal surface of the projections 77, there are spacers 100 (FIG. 1) for aligning the battery-blower unit 55.

The bottom member 41 is a liquid-tight tray (FIGS. 1,2,4). The base 111 of the tray extends beyond its vertical walls 113 on one side, providing a shelf-like surface 115 (FIG. 2) on one side. Projections 117 extend along opposite ends of the base of the tray.

In the center of the tray there is a ring 121. A plurality of studs 123, 125 and 127 arrayed in rows generally perpendicular to each other project upwardly from the base 111. The studs 123 are short, the studs 125 which are near the corners of the array are longer and the studs 127 which project integrally from the wall 113 are of the same length as the studs 125.

FIG. 1 shows the can 43 supported on the short studs 123 and spaced from the walls 113 by being nested in the upward projecting studs 125 in the corners (FIGS. 1, 2). The can 43 is thus prevented from moving. The air which vaporizes the liquid in the wick 45 thus has space for unobstructed flow. As shown in FIG. 4, the ceramic discs 131 are mounted in one orientation and the wafers 133 are mounted in an orientation at right angles to the ceramic discs. The ceramic discs 131 and wafers 133 are spaced by the studs so that air circulates from the battery-blower unit 35 contacts these components on all sides to diffuse the deodorant vapors. Studs 123 in a rectangular array, and studs 125 and 127 are provided to position and hold erect the wafers 133, typically four number, aligned and ceramic discs 131, typically three in number, aligned generally at right angles to the wafers.

The battery-blower unit 35 (FIG. 3) includes the supporting plate 171 and the battery motor bracket 173. The supporting plate 171 is rigidly mounted on the back plate 37. The outer sides 175 of the supporting plate 171 are thrust upwardly through the runners 93 (FIGS. 1,3,4,6), while the inner surface of the plate at the bottom rides on the ramps 91. This inner surface is flexed and is under stress when insertion takes place. When the inner surface of the plate 171 springs from the ramps 91, the plate 171 is snap-locked to the back plate 37. The runners 93 and the plate 171 at its ends are a tight fit so that the passage of the ends of the plate through the runners is resisted and the plate 171 is flexed. Once plate 171 is fully positioned in the runners, it relaxes producing a snap-lock. The plate 171 is also held by pins 188 which extend from top member 39 (FIGS. 1). The plate 171 is aligned by the spacers 100 in the projections 77 of back plate 37. Near the top, channels 170 and 172 extend from opposite ends of support plate 171 spaced a short distance outwardly from positive pole and the negative pole respectively (FIG. 3). The flanges of channel 170 are spaced further apart than the flanges of channel 172 to permit the necessary close spacing of channel 170 and the protruding positive pole 174. This structure also precludes improper positioning of the battery. If an attempt were made to position the battery with the positive pole opposite channel 170, there would be no contact with negative battery terminal, necessitating correct polarization for operation of the battery-blower unit 35.

The battery-blower bracket 173 includes a cradle 176 for the battery 177 (FIG. 1). A motor socket unit 179 extends from the cradle 176. The cradle 176 includes plates 181 whose opposite vertical surfaces 183 are arcuate to provide seats for the battery 177. The arcuate seats 183 for the battery 177 in opposite surfaces constitute a cradle for the battery in each of opposite mountings vertically of the battery-b lower bracket 173. To hold the battery 177 securely, the supporting plate 171 is provided with holding bars 184 which have curved edges 185 to match the contour of the battery. The holding bars 184 are seated in the right angle joint formed between the outer perimeter 178 of the supporting plate 171 and projecting shelf 180 part of a frame-like structure 182 internally of plate 171. The motor socket unit 179 is supported by projections 186 connected to the outer ends of the plates 181. The motor-socket unit 179 includes a socket 187 for a motor of larger dimensions and a socket 189 for a motor 191 of smaller dimensions. In FIG.3 the motor 191 is shown in its socket 189. The drive shaft 193 of the motor is connected to drive fan 195 having blades 57. The sockets 187 and 189 are connected back-to-back so that each can be above or below as bracket 173 is oriented. The socket 187 includes an internal annular surface 197 (FIG. 8) which may be arcuate for supporting the motor of larger dimensions. The motor 191 of smaller dimensions is supported in a ring 201 (FIG. 8) under or above the surface 197 depending on how the bracket 173 is oriented. The motor of larger dimensions is held in the socket 187 by friction and the motor 191 of smaller dimensions is held in the ring 201 by a lip 202 along the outer edge of socket 189 (FIG. 9).

The supporting plate 171 has a generally central opening 205 having a generally rectangular boundary. Along opposite vertical sides of the boundary there are tracks 207. The tracks 207 extend only partly along the opposite sides (FIGS. 4,8,9). At the end of the battery-motor bracket 173, remote from the socket unit 179, the bracket has opposite slots 209 dimensioned and spaced to engage the tracks 207. To mount the battery-blower bracket 173 on the supporting plate 171, the slots 209 are engaged with the track 207 at the points 211 where the tracks terminate,i.e., at the bottom when the supporting plate is mounted on the back plate 37, and are moved along the track (FIG. 4). When the slots 209 reach the ends 213 of the tracks 207, they are stopped by the body of the supporting plate 171. The slots 209 are a tight fit on the track 207 and they are stressed while being moved. When the movement is stopped, the slots are relaxed and the bracket 173 is snap-locked on the support plate 171. In addition, the slotted members 209 are forced over the lower bar 190 of the frame 182 and when they clear the inner end 172 of the bar 190 spring into snap lock state. The forced movement of the bracket continues and the ends of-the slot 209 spring over edge 194 producing an additional snap lock. The slots 209 are interchangeable with the tracks 207 so that the bracket 173 can be mounted with the socket 1 89 below the socket 187 or the socket 189 above and the socket 187.

The channels 170 and 172 extending from support plate 171 serve to connect the leads or wires 215 from motor.191 or-a motor i n the socket 187 to the battery 177.. The wires 215 are guided by nubbins 216 on plates 181 of batter y cradle 176 (FIGS. 3,8). Each channel 170 and 172 has a hole 217 in its inner end (FIG. 6,7). The stripped end 219 of each wire 215 from the motor terminals (not shown) is passed through this hole (FIG. 7) and extends inwardly of the channels 170 and 172. A metal strip 223 (FIGS. 3,7) is inserted in the slots 225, formed by the flanges 227 and 228 of the channels. Each strip 223 firmly engages the stripped end 219 of a wire 215 and it has a bulge 229 which engages the adjacent pole 231 of the battery. Each wire is thus connected to a pole of the battery.

As shown in FIG. 8, the supporting plate 171 and the battery-motor unit 173 are formed in twin molds. The components 171 and 173 are formed typically of a material such as acrylic butylene and styrene. This material serves to produce a structure of greater strength than the polypropylene fiberglass typical of the material from which the other components such as the back plate 37, the top member 39 and the bottom member 41 are formed. The additional strength is necessary because the components 171 and 173 are subjected to higher stresses by the moving parts which they support. The components 171 and 173 are positioned in the mold so that they can be readily removed and snapped together to produce a sturdy motor-battery holder assembly.

While preferred embodiments of this invention have been disclosed herein, many modifications thereof are feasible. This invention is not to be restricted except insofar as is necessitated by the spirit of the prior art.

We claim:

1. For combination in a frame for receiving the housing of a deodorant cabinet, a drive for producing an air stream including a socket assembly having back-to-back mounted sockets for receiving motors of different dimensions and reversible means for mounting said socket assembly selectively for combination in said frame with either socket positioned to receive its corresponding motor fixedly for producing an air stream.

2. The drive of claim 1 wherein the reversible mounting means includes a cradle for supporting a battery and means for connecting the battery in energizing relationship with a motor in either socket.

3. The drive of claim 1 wherein the socket assembly is mounted with the sockets positioned each to suspend its corresponding motor vertically, the socket for the motor of larger dimensions being dimensioned to hold its motor by friction and the socket for the motor of smaller dimensions being provided with physical means to hold the motor of smaller dimensions.

4. For combination in deodorant apparatus having support means, a drive for producing an air stream, said drive including an integrated socket assembly including a first socket adapted to receive a motor of larger dimensions and a second socket adapted to receive a motor of smaller dimensions, and means, cooperative with said support means, for mounting said socket assembly selectively with said first or second socket positioned to receive the corresponding larger or smaller motor fixedly energizably.

5. The drive of claim 4 wherein the drive includes a battery, said drive being characterized by conductor means connected to the battery for energizing the motor which is selectively adapted to be received in the first socket or the second socket, said conductor means being adapted to be connected to said motor which is selectively adapted to be received in said first socket or said second through said second socket or said first socket which is not selectively adapted to receive a motor.

6. For combination in a frame for receiving the housing of a deodorant cabinet, a drive for producing an air stream including a socket assembly having back-to-back mounted sockets for receiving motors of different dimensions and reversible means for mounting said socket assembly selectively for combination in said frame with either socket positioned to receive its corresponding motor fixedly for producing an air stream, said reversible mounting means including a bracket having oppositely disposed tracks therein and said socket assembly including runners reversibly engagable with said tracks in said assembly.

7. The drive of claim 6 wherein the bracket includes snap locking means cooperative with the runners for snap locking the socket assembly on said bracket.

8. The drive of claim 7 wherein the runners are composed of a flexible material and the locking means include means on said bracket for flexing said runners as they move into engagement with the tracks and for relaxing the flexing when the runners reach the locking position whereby the runners snap into locking position.

9. The drive of claim 6 wherein the bracket including the tracks and socket assembly including the runners are composed of a flexible plastic comprising predominantly acrylic butylene and styrene.

10. For combination in deodorant apparatus having support means having resilient snap means, a drive for producing an air stream, said drive including an integrated socket assembly including a first socket adapted to receive a motor of larger dimensions and a second socket adapted to receive a motor of smaller dimensions, said drive also having resilient snap means, said resilient snap means of said drive being adapted to cooperate with said resilient snap means of said support for mounting said socket assembly selectively with said first or second socket positioned to receive the corresponding larger or smaller motor fixedly energizably.

* * * * *